United States Patent [19]

Yodice et al.

[11] Patent Number: 5,015,402

[45] Date of Patent: May 14, 1991

[54] BASIC METAL DIHYDROCARBYLPHOSPHORODITHIOATES

[75] Inventors: Richard Yodice; Alan C. Clark, both of Mentor, Ohio

[73] Assignee: The Lubrizol Corporation, Wickliffe, Ohio

[21] Appl. No.: 426,512

[22] Filed: Oct. 24, 1989

Related U.S. Application Data

[63] Continuation of Ser. No. 140,380, Jan. 4, 1988, abandoned, which is a continuation-in-part of Ser. No. 928,422, Nov. 7, 1986.

[51] Int. Cl.$^5$ ................ C10M 135/00; C10M 137/00
[52] U.S. Cl. ................ 252/32.7 E; 252/46.4; 252/46.7; 252/49.3
[58] Field of Search ............. 252/32.7 E, 36, 46.7, 252/49.3, 46.4, 400.21, 400.22; 556/25

[56] References Cited

U.S. PATENT DOCUMENTS

| | | | |
|---|---|---|---|
| 2,552,570 | 5/1951 | McNab et al. | 252/32.7 |
| 2,794,780 | 6/1957 | Wystrach et al. | 252/32.7 |
| 2,797,238 | 6/1957 | Miller et al. | 260/500 |
| 3,290,246 | 12/1966 | Perotti et al. | 252/32.7 |
| 3,290,347 | 12/1966 | Miller | 556/25 |
| 3,347,790 | 10/1967 | Meinhardt | 252/32.5 |
| 3,413,327 | 11/1968 | Gordon | 260/429.9 |
| 3,428,662 | 2/1969 | Millendorf et al. | 260/429.9 |
| 3,595,792 | 7/1971 | Elliot et al. | 252/32.7 E |
| 3,691,220 | 9/1972 | Horodysky | 260/429.9 |
| 3,843,530 | 10/1974 | Niedzielski | 252/32.7 E |
| 4,085,053 | 4/1978 | Caspari | 252/32.7 E |
| 4,094,800 | 6/1978 | Warne | 252/32.7 E |
| 4,101,428 | 7/1978 | Crawford | 252/32.7 E |
| 4,123,370 | 10/1978 | Meinhardt | 252/32.7 E |
| 4,308,154 | 12/1981 | Clason et al. | 252/32.7 E |
| 4,376,711 | 3/1983 | Shaub | 252/32.7 E |
| 4,377,527 | 3/1983 | Sabol et al. | 260/429.9 |
| 4,392,966 | 7/1983 | Schlicht | 252/32.7 E |
| 4,466,895 | 8/1984 | Schroeck | 252/32.7 E |
| 4,495,075 | 1/1985 | Buckley | 252/32.7 E |
| 4,507,215 | 3/1985 | Schroeck | 252/32.7 E |
| 4,582,920 | 4/1986 | Bridger | 556/25 |
| 4,704,216 | 11/1987 | Hata et al. | 252/32.7 E |

FOREIGN PATENT DOCUMENTS 0024146  1/1980  European Pat. Off. .
717039  10/1954  United Kingdom .

OTHER PUBLICATIONS

Burn et al., "The Structure of Basic Zinc O, O-Dialkyl Phosphorodithioates", Chemical Communications, No. 17, pp. 394–396 (1965).
Wystrach et al., "Basic Zinc Double Salts of O, O-Dialkyl Phosphorodithioic Acids", Journal of Organic Chemistry; vol. 21, pp. 705–707 (1956).
Burn et al., "EXAFS Determination of the Structure of Basic Zinc O O-Di-n-butyl Phosphorodithioate", Journal of the Chemical Society, Chemical Communication, pp. 982–984 (1986).

*Primary Examiner*—Margaret B. Medley
*Attorney, Agent, or Firm*—Neil A. DuChez; Frederick D. Hunter; Forrest L. Collins

[57] ABSTRACT

Basic metal dihydrocarbylphosphorodithioates and phosphoromonothioates are prepared by employing a catalytic amount of an alkali metal or alkaline earth metal hydroxide or mixtures thereof. Also basic, multiple metal complexes of various dihydrocarbylphosphorodithioic acids have been developed. These salts and complexes are highly effective antiwear and antioxidant additives for functional fluids, e.g., lubricating oils.

41 Claims, No Drawings

BASIC METAL DIHYDROCARBYLPHOSPHORODITHIOATES

This application is a continuation of U.S. Application Ser. No. 07/140,380, filed Jan. 4, 1988, now abandoned, which was a continuation-in-part of U.S. Application Ser. No. 06/928,422, filed Nov. 7, 1986. These prior applications are incorporated herein by reference in their entireties.

INTRODUCTION TO THE INVENTION

This invention relates to basic metal dihydrocarbylphosphorodithioates which impart effective antiwear properties and antioxidant properties to functional fluids such as lubricants, and to fuels. The invention also relates to a method for preparing basic mixed metal dihydrocarbylphosphorodithioates.

Alkali metal hydroxides and specifically sodium hydroxide have been used in the preparation of various metal dihydrocarbylphosphorodithioates, such as zinc dialkyldithiophosphates. Stoichiometric amounts of the alkali metal hydroxides have been reacted with phosphorus-containing acids to form salts; these salts can subsequently be reacted with zinc chloride and the like to prepare the desired dihydrocarbyldithiophosphate. Such methods and variations thereof are illustrated in U.S. Pat. No. 2,794,780 to Wystrach et al; U.S. Pat. No. 2,797,238 to Miller et al; U.S. Pat. No. 3,843,530 to Niedzielski; and U.S. Pat. No. 4,123,370 to Meinhardt. U.S. Pat. No. 2,797,238 to Miller et al discloses the preparation of various phosphinodithioic metal compounds, including zinc compounds, utilizing a stoichiometric amount of sodium hydroxide.

U.S. Pat. Nos. 3,347,790 and 4,089,793 to Meinhardt disclose generally the preparation of various zinc dialkyldithiophosphate compounds, including "normal" or "neutral" compounds and "basic" compounds.

U.S. Pat. No. 4,094,800 to Warne discloses a basic zinc dialkyldithiophosphate derived from primary alcohols containing from about 6 to about 20 carbon atoms.

In U.S. Pat. No. 4,466,895 to Schroeck metal salts of one or more dialkylphosphorodithioic acids are disclosed that contain specific alkyl groups.

Mixed metal salts of dialkylphosphorodithioic acids and carboxylic acids are disclosed in U.S. Patent 4,308,154 to Clason et al.

The ammonia catalyzed preparation of zinc dihydrocarbyldithiophosphates is disclosed in U.S. Pat. No. 4,377,527 to Sabol et al.

U.S. Pat. No. 4,495,075 to Buckley discloses a method for preventing the precipitation of zinc dialkyldithiophosphates, which contain a high percentage of lower alkyl group, from functional fluids.

The preparation of a mixture of zinc salts of O,O-dialkyldithiophosphoric acids are disclosed in U.S. Pat. No. 4,101,428 to Crawford.

Lubricants containing zinc dithiophosphates which exhibit both antiwear and antioxidant properties are disclosed in U.S. Pat. No. 3,290,246 to Perotti et al.

U.S. Pat. No. 2,552,570 to McNab et al, U.S. Pat. No. 4,582,920 to Bridges, and European Patent 24146, granted Oct. 9, 1985 to Exxon Research and Engineering Company, each disclose copper salts of phosphorus- and sulfur-containing acids.

Other salts, and processes for their production, are the subjects of U.S. Pat. No. 3,428,662 to Millendorf et al, U.S. Pat. No. 3,595,792 to Elliot et al, U.S. Pat. No. 4,085,053 to Caspari, U.S. Pat. No. 4,376,711 to Shaub, and U.S. Pat. No. 4,392,966 to Schlicht.

Basic zinc O,O-dialkylphosphorodithioates are discussed in papers by: Burn et al, "The Structure of Basic Zinc O O-Dialkyl Phosphorodithioates", *Chemical Communications*, No. 17, pp. 394-396 (1965); Wystrach et al, "Basic Zinc Double Salts of O, O-Dialkyl Phosphorodithioic Acids", *Journal of Organic Chemistry*, Vol. 21, pp. 705-707 (1956); and Burn et al, "EXAFS Determination of the Structure of Basic Zinc 00-Di-n-butyl Phosphorodithioate" *Journal of the Chemical Society, Chemical Communication*, pp. 982-984 (1986).

SUMMARY OF THE INVENTION

In accordance with the present invention, a novel method for preparing basic mixed metal dihydrocarbylphosphorodithioate compounds and complexes has been discovered. Further in accordance with the invention, novel basic, multiple metal complexes of the dialkylphosphorodithioates have been developed. Still further in accordance with the present invention, it has been found that the basic mixed metal dialkylphosphorodithioates and complexes thereof are useful as highly effective antiwear and antioxidant additives for functional fluids, including lubricant and fuel compositions. Still further in accordance with the present invention, a method for preparing basic mixed metal dihydrocarbylphosphorodithioates in the absence of a catalyst or promoter is provided. Still further in accordance with the invention, various functional fluids, including lubricants, automatic transmission fluids, hydraulic fluids and the like, comprising basic mixed metal dihydrocarbylphosphorodithioates and complexes thereof of the present invention are provided.

In accordance with one aspect of the invention, a basic metal dihydrocarbylphosphorodithioate is prepared by reacting (A) at least one dihydrocarbylphosphorodithioic acid, or a normal acid metal salt thereof, with (B) at least one metal salt thereof, with (B) at least one metal oxide or hydroxide, wherein the metal is zinc, copper, nickel, chromium, iron, cobalt, manganese, calcium, barium, antimony, lead, aluminum, or tin in the presence of (C) a catalytic amount of at least one alkali metal or alkaline earth metal hydroxide oxide, carbonate, or halide, wherein the metal of (C) is different from the metal of (B).

These and other aspects of the invention will become more clear to those skilled in the art upon the reading and understanding of the following specification.

DETAILED DESCRIPTION OF THE INVENTION

A novel method for preparing basic metal dihydrocarbylphosphorodithioates and complexes thereof has been developed. In one embodiment of the invention, the method involves employing a catalytic amount of: at least one alkali metal hydroxide, oxide, carbonate or halide; or at least one alkaline earth metal hydroxide, oxide, carbonate or halide, or mixtures thereof. The method further involves reacting at least one dihydrocarbylphosphorodithioic acid or the normal or acid metal salt of at least one of these acids with a metal oxide, or hydroxide, wherein the metal is selected from zinc, copper, nickel, chromium, iron, cobalt, manganese, barium, calcium, lead, antimony, aluminum or tin in the presence of a catalytic amount of at least one alkali metal hydroxide, oxide, halide or carbonate, or alkaline earth metal hydroxide, oxide, halide or carbonate; or mixtures thereof. It should be recognized that the metal of the catalyst will not be the same as the metal of the metal-containing reactant, e.g., when the reactant is a calcium or barium salt.

The term "catalytic amount", as used herein, denotes an amount of a material which promotes the efficient reaction of a dihydrocarbylphosphorodithioic acid, or salt, with a metal-containing reactant to form a basic salt; in general, a catalytic amount contains about 0.001 to 0.05 equivalents of an alkali or alkaline earth metal, per equivalent of phosphorus in the acid or its salt.

Another embodiment of the invention involves the preparation of basic metal dihydrocarbylphosphorodithioates by contacting a normal or acid metal salt of a dihydrocarbylphosphorodithioic acid with a metal-containing reactant in the absence of a catalyst or promoter. This aspect of the invention has been found to be particularly useful for preparing basic metal dihydrocarbylphosphorodithioates where the hydrocarbyl groups are aryl, aralkyl or long chain alkyl (e.g., greater than 24 carbon atoms).

As still another aspect of the invention, basic, multiple metal complexes of dialkylphosphorodithioic acids have been developed and may be represented by the following general formula:

$$[Z]_d[(RO)_2PSS]_y M_a X_b \qquad (I)$$

wherein M and X represent different metal cations selected from the group consisting of zinc, copper, chromium, iron, copper, manganese, calcium, barium, lead, antimony, tin and aluminum; Z is an anion selected from oxygen, hydroxide and carbonate; R is independently a linear or branched alkyl group of 1 to about 200 carbon atoms, or a substituted or unsubstituted aryl group of 6 to about 50 carbon atoms; a and b are integers of at least one and are dependent upon the respective oxidation states of M and X; y is a whole integer which is dependent upon the oxidation states of M and X; and d is an integer of 1 or 2.

As used herein, the terms "hydrocarbyl" or "hydrocarbon-based" denote a radical having a carbon atom directly attached to the remainder of the molecule and having predominantly hydrocarbon character within the context of this invention. Such radicals include the following:

(1) Hydrocarbon radicals; that is, aliphatic, e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the together form an alicyclic radical).

(2) Substituted hydrocarbon radicals; that is, radicals containing non-hydrocarbon substituents which, in the context of this invention, do not alter the predominantly hydrocarbon character of the radical. Those skilled in the art will be aware of suitable substituents; examples are halo (particularly chloro and fluoro), alkoxy, mercapto, nitro, nitroso, sulfoxy, and other groups.

(3) Hetero radicals; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

Terms such as "alkyl-based radical", "aryl-based radical" and the like have meaning analogous to the above with respect to alkyl and aryl radicals and the like.

The preferred radicals are usually hydrocarbon, that is, composed most often of carbon and hydrogen atoms, and are straight- or branched-chain alkyl.

By "basic" metal phosphorodithioate, it is intended, for the purposes of the present invention, to include those salts and/or complexes that have a higher ratio of equivalents of total metal to equivalents of the dihydrocarbylphosphorodithioic acid moiety, than that of the corresponding "neutral" or "normal" salt and/or complex. Partially neutralized dihydrocarbyl phosphorodithioic acids, denoted "acid salts" herein, have a lower ratio of equivalents than that of the "Neutral" or "normal" salts. More specifically, a "neutral" or "normal" zinc phosphorodithioate has one equivalent of zinc per one equivalent of the phosphorodithioic acid moiety, i.e., a 1:1 ratio in this case. The corresponding "basic" zinc phosphorodithioate has more than one equivalent of zinc per one equivalent of the phosphorodithioic acid moiety, e.g., in certain instances the equivalent ratio will be 4:3 of zinc to phosphorodithioate.

In a preferred embodiment of the present invention, the salts and/or complexes of the present invention are derived from oxides or hydroxides of a metal selected from the group consisting of Zn, Cu, Ca, Ba, Ni, Cr, Fe, Co, Mn, Sn, Sb or mixtures thereof. In a most preferred embodiment, metal oxides are used and the metal is selected from Zn, Cu, Ca, Sb, Co or mixtures thereof.

Also in a preferred embodiment, the catalyst used in the method of the present invention is calcium hydroxide, potassium hydroxide or sodium hydroxide. In a most preferred embodiment, the catalyst is sodium hydroxide.

In a further preferred embodiment, the hydrocarbyl groups of the phosphorodithioic acid are, independently, linear or branched alkyl groups of 1 to about 200 carbon atoms or substituted or unsubstituted aryl group of 6 to about 50 carbon atoms. Representative of such alkyl or aryl groups include octyl, butyl, pentyl, propyl, oleyl, heptyl, hexyl, heptylphenyl, dodecylphenyl, nonylphenyl, cresyl and the isomers thereof. In a more preferred embodiment, the total number of carbon atoms in the dihydrocarbylphosphorodithioate moiety is at least 8. In a most preferred embodiment, the hydrocarbyl groups are, independently, selected from isooctyl, isopropyl, 4-methyl-2-pentyl and heptylphenyl.

With respect to the multiple metal complexes of the present invention, it has been found that the complex includes at least two different metals where one metal is included as the oxide or hydroxide and the other metal is included in the form of a salt of a phosphorodithioic acid, generally in a 1:3 molar ratio. More specifically, one mole of a metal oxide, for example, is complexed with 3 moles of a neutral metal dihydrocarbylphosphorodithioate. This ratio, of course, may vary dependent upon the ratio of reactants used to prepare the complex and the like.

A presently preferred basic salt for use in lubricating compositions is a mixed zinc and copper salt of a dihydrocarbylphosphorodithioic acid. This salt can be conveniently prepared by reacting a normal or acid zinc salt of the acid with a cuprous compound, such as cuprous oxide, in the presence of a catalytic amount of a material such as sodium hydroxide.

When the method of the invention is carried out in the absence of a catalyst, the reaction is conducted by contacting a metal dihydrocarbylphosphorodithioate with a metal oxide. The metal of the phosphorodithioate and the metal of the oxide may be the same or different and preferably are, independently, Zn, Cu, Ca, Sb and Co. This embodiment of the invention is most effective in preparing "basic" metal dihydrocarbylphosphorodithioates where at least one hydrocarbyl group is aralkyl, e.g., heptylphenyl or dodecylphenyl, or is long-chain alkyl, e.g., greater than 24 carbon atoms.

The following examples are provided to illustrate various salts/complexes prepared by the method of the present invention as described above. These examples are provided for illustrative purposes only and are not to serve as a limitation on the scope of the invention, such scope being set out solely in the appended claims.

EXAMPLE I 354 grams of zinc oxide and 225 grams of diluent oil were charged to the reaction container. At ambient temperature, 5.28 grams of a 50% sodium hydroxide solution was charged with stirring to the reaction container. After which, 1,982 grams of zinc O,O-isobutyl-/amyl (65:35) dithiophosphate was charged to the reaction container. After the initial exotherm, the reaction container was heated to 80° C. and held at that temperature for 5 hours. The material was vacuum stripped at 100° C. and 10mmHg. After filtering, 1,773 grams of product resulted.

EXAMPLE II 1,030 grams of zinc diheptylphenyldithiophosphate, 1.6 grams of a 50% sodium hydroxide solution, 50 grams of water and 32.1 grams of zinc oxide were charged to a reaction container with stirring. This mixture was heated to 80° C. and held at that temperature. After filtering, 982.1 grams of product was produced.

EXAMPLE III

To a reaction container was charged 369 grams of zinc oxide and 309 grams of diluent oil. With stirring 4.8 grams of 50% sodium hydroxide solution was charged to the reaction container. After the addition was complete, 2,472 grams of zinc diisooctyldithiophosphate was charged to the reaction container. The reaction container was heated to 80° C. and held at that temperature for 5 hours. After vacuum stripping at 100° C. and 20mmHg, the material was filtered to yield 2,383 grams of product.

EXAMPLE IV

A reaction container was charged with 147 grams of zinc diisooctyldithiophosphate, 4.1 grams of calcium hydroxide and 10 grams of water. The mixture was heated to 95° C. and maintained at that temperature for 5 hours. The mixture was vacuumed stripped under reduced pressure at 110° C. Final product yielded 148 grams after filtering through diatomaceous earth filter aid.

EXAMPLE V

A reaction container was charged with 1,945 grams of zinc dialkyldithiophosphate (the alkyl groups are a 65/35 mixture of isobutyl/primary amyl respectively), 77 grams of calcium hydroxide, 22 grams of water and 700 grams of toluene. This mixture was stirred and heated to 80° C. and maintained at the temperature for 5 hours. The contents were then vacuum stripped at 100° C. and 10mmHg. The product was filtered through diatomaceous earth filter aid yielding 2,000 grams of product.

EXAMPLE VI

The same procedure in the previous examples was followed utilizing 11 grams of calcium hydroxide, 10 grams of water and 291.4 grams of zinc dialkyldithiophosphate (the alkyl groups were a 65/35 mixture of isobutyl/amyl respectively). 250 grams of product was obtained.

EXAMPLE VII

A reaction container was charged with 1,000 grams of zinc diisooctyldithiophosphate, 26.88 grams of copper (I) oxide, 2.54 grams of a 50% sodium hydroxide solution and 25.4 grams of distilled water. This mixture was heated with stirring to 80° C. and maintained at that temperature for 2.5 hours. The reaction mixture was then vacuumed stripped at 100° C. and 15mmHg. The mixture was then filtered through diatomaceous earth filter aid to obtain 1,022 grams of product.

EXAMPLE VIII

A reaction container was charged with 30.1 grams of copper oxide, 2.0 grams of a 50% solution of sodium hydroxide, 25 grams of water and 350 grams of zinc dialkyldithiophosphate (the alkyl groups are a 65/35 mixture of isobutyl/amyl respectively). This mixture was heated to 100° C. and maintained at that temperature for 1.5 hours. The mixture was then vacuum stripped and filtered through diatomaceous earth filter aid to give 320 grams of product.

EXAMPLE IX

The procedure for the above examples was followed to prepare the following product which was prepared from 34 grams of zinc oxide, 18 grams of copper (I) oxide, 33 grams of diluent oil and 256 grams of a dialkyldithiophosphoric acid (the alkyl groups are a 60/40 mixture of methylamyl/isopropyl, respectively). The addition of these reactants took place over a period of 1.5 hours where the temperature was maintained at less than 60° C. After the addition was complete, the mixture was heated to 75° C. and maintained at that temperature for 4.5 hours. After filtering through diatomaceous earth filter aid, 270 grams of product was obtained.

EXAMPLE X

The same procedure was followed as with the previous examples where the following reactants were used to prepare the desired product. 483 grams of a 1:1.1 equivalents mixture of diisooctyldithiophosphoric acid and copper (I) oxide, 13.43 grams of zinc oxide and 9.6 grams of distilled water. From this reaction mixture was obtained 450 grams of product.

EXAMPLE XI

A one liter reaction container was charged with 32 grams of diluent oil and 25 grams of zinc oxide. 200 grams of di-4-methyl-2-pentyldithiophosphoric acid were added dropwise to the reaction mixture over a period of one hour. This mixture was then heated to 65° C. and maintained at that temperature for one hour. After this one-hour period, 22 grams of manganese carbonate were added to the reaction mixture. This addition was followed by the addition of an additional 60 grams of di-4-methyl-2-pentyldithiophosphoric acid. This final reaction mixture was heated to 75° C. and maintained at that temperature for 4 hours. The reaction mixture was then vacuum stripped at 95° C. and 10mmHg and filtered through diatomaceous earth filter aid. 242 grams of the mixed metal product was obtained.

The salts and complexes according to the present invention, which specific species have been illustrated in the above Examples I-XI, are versatile additives for lubricating compositions and fuels as well as other functional fluids. The compositions of the present invention are useful additives for imparting antioxidant properties and antiwear properties to various lubricant compositions. The complexes, i.e., additives, of the present invention also find use in functional fluids including fuel compositions, automatic transmission fluids, hydraulic fluids and the like. The salts and complexes of the present invention may also be used as curing agents for epoxy resins and the like.

The additives of the present invention may be formulated with a functional fluid by the direct blending of the composition to the particular functional fluid, e.g., lubricating oil, or it may be formulated with the functional fluid in the form of a concentrate. Such a concentrate may be prepared by adding 1% to about 99% by weight of the composition or additive of the present invention to a substantially inert, normally liquid organic diluent or solvent such as benzene, toluene, xylene, petroleum naphtha, mineral oil, ethylene glycol monomethyl ether or the like.

The compositions of the present invention, formulated with the particular functional fluid or concentrate, may contain other additives and chemistries such as dispersants, antioxidants and the like. Such other additives and chemistries include, for example, detergents and dispersants of the ash-producing or ashless type, corrosion- and oxidation-inhibiting agents, pour point depressing agents, extreme pressure agents, color stabilizers, antifoam agents and VI improvers. These other additives and chemistries are fully described and disclosed in U.S. Pat. Nos. 3,541,014, 4,289,635, and 4,266,945, which disclosures of these patents relating to such other additives and chemistries are hereby incorporated by reference for such disclosures.

A preferred dispersant for use with the present invention is at least one substituted succinic acid or derivative thereof containing of substituent groups, wherein the substituent groups are derived from poly-alkylene, said polyalkylene being characterized by a Mn value of 500 to about 10,000 and a Mw/Mn value of 1.0 to about 4.0.

It has also been found that the additive compounds of the present invention are useful in formulating various lubricant compositions. The salt and/or metal complex additives of the present invention are useful in both mineral and synthetic lubricating oils and greases. Synthetic oils include polyolefin oils (e.g., polybutene oil, decene oligomer, and the like), synthetic esters (e.g., dinonyl sebacate, trioctanoic acid ester of trimethylolpropane, and the like), polyglycol oils, and the like. Greases are made from these oils by adding a thickening agent such as sodium, calcium, lithium, or aluminum salts of fatty acids such as stearic acid. These and similar thickening agents are described in U.S. Pat. Nos. 2,197,263, 2,564,561 and 2,999,066. The oils and greases of the present invention are prepared by blending an amount of at least one salt or metal complex additive of the present invention sufficient to impart antiwear properties and antioxidant properties into the oil or grease. A useful concentration may range from about 0.1 to about 5 weight percent.

To further illustrate various functional fluid compositions, specifically lubricant compositions, comprising the salts and complexes of the present invention, the following illustrative examples are provided. It is again pointed out that the following examples are provided for illustrative purposes only and are not to place any limitation on the scope of the invention where such scope is set out only in the claims. All parts and percentages are by weight.

Typical compositions according to this invention are listed in the following table.

TABLE I

| COMPONENTS | A | B | C | D | E | F |
|---|---|---|---|---|---|---|
| Base Oil | 90.37 | 90.87 | 92.82 | 95.0 | 81.13 | 83.18 |
| Product of Example I | | | | | | 2.00 |
| Product of Example III | 0.11 | 0.11 | 3.86 | 2.50 | | |
| Product of Example VIII | | | | | 2.60 | |
| Reaction Product of Polybutenyl Succinic Anhydride with Ethylene Polyamine | | | | | 3.61 | 2.50 |
| Reaction Product of Polybutenyl Succinic Anhydride with Ethylene Polyamine and Pentaerythritol | | | | | | 2.50 |
| Reaction Product of Polybutenyl Succinic Anhydride with Ethylene Polyamine and Carbon Disulfide | 2.00 | 2.00 | | | | |
| Reaction Product of Polybutenyl Succinic Anhydride with Ethylene Polyamine and | 1.00 | 1.00 | | | | |

TABLE I-continued

| COMPONENTS | A | B | C | D | E | F |
|---|---|---|---|---|---|---|
| Boric Acid | | | | | | |
| Basic Calcium Alkylbenzenesulfonate | 1.79 | 1.79 | | | | 1.10 |
| Basic Magnesium Alkylbenzenesulfonate | | | | | 1.35 | 0.65 |
| Reaction Product of Maleic Anhydride-styrene Copolymer with Alcohol and Amine | 3.50 | 3.50 | 1.11 | | 0.20 | |
| Hydrogenated Styrene-diene Block Copolymer Viscosity Improver | | | | 9.00 | | |
| Ethylene-propylene Copolymer Viscosity Improver | | | | | | 7.00 |
| Sulfurized Fat | 0.50 | | | | | |
| Reaction Product of an Organo Sulfur Cmpd. with an Epoxide | 0.50 | 0.50 | | | | |
| Sulfurized Olefin | | | 0.17 | 2.50 | 1.50 | 0.06 |
| Ester of Dimercaptothiadiazole | | | | | 0.10 | |
| Sulfurized Diels-Alder Adduct | | | | | | 0.60 |
| Oil Soluble Phosphorus-Containing Extreme Pressure Agent | | | 1.47 | | | |
| Alkylated Arylamine | 0.10 | 0.10 | | | 0.50 | 0.30 |
| Ethoxylated Fatty Amine | 0.09 | 0.09 | | | | |
| Fatty Amide | | | 0.11 | | | 0.10 |
| Fatty Amine | | | 0.39 | | | |
| Silicone Antifoam Agent | 0.042 | 0.042 | 0.066 | | 0.006 | 0.006 |

The products of the various examples, contained in a fully formulated lubricating composition as is described in Table I, were tested with regard to a Timken "OK" load test as well as a contact pressure test in accordance with ASTM D 2782, with the exception that in the "OK" load test the following procedural differences were made:

1. Test cup and block surfaces are merely "wetted" with test lubricant (approximately 5 drops on block). No test sample is recirculated over the surfaces during the test.
2. Test duration is 5 minutes under load.
3. This procedure is run as an "OK" Load test, determining "OK" Load as in ASTM Test D 2782 except utilizing the following load increments:
    a. "OK" Load is less than or equal to 20 lbs.: Determine "OK" Load to the nearest 1 lb.
    b. "OK" Load is greater than 20 lbs.: Determine "OK" Load using standard load increments as described in ASTM Test D 2782.

The results from testing products of the present invention according to the above test procedure are set out in Table II below.

TABLE II

| No. Sample | Timken Results OK Load (lbs.) | Unit Press. psi. | Wt %[1] P |
|---|---|---|---|
| 1. Product of Example IV | 15 | 16,350 | 0.05 |
| 2. Product of Example V | 17 | 7,850 | 0.05 |
| 3. Product of Example VI | 15 | 7,625 | 0.05 |

[1] Based on the weight of the phosphorous content on the sample.

Products of the present invention illustrated in the above examples were also tested in the copper strip test in accordance with ASTM D 130. The results from testing products of the present invention according to the above test procedure are set out in Table III below.

TABLE III

| Example No. | Copper Strip |
|---|---|
| V | 1a |
| VI | 1a |
| VII | 2b-2c |
| IX | 1a |

The invention also includes aqueous compositions characterized by an aqueous phase with at least one salt or complex of the present invention dispersed or dissolved in said aqueous phase. Preferably, this aqueous phase is a continuous aqueous phase although, in some embodiments, the aqueous phase can be a discontinuous phase. These aqueous compositions usually contain at least about 25% by weight water. Such aqueous compositions encompass both concentrates containing about 25% to about 80% by weight, preferably from about 40% to about 65% water; and water-based functional fluids containing generally over about 80% by weight of water. The concentrates generally contain from about 10% to about 90% by weight of at least one of the salt or complex materials of the invention. The water-based functional fluids generally contain from about 0.05% to about 15% by weight of the salt or complex materials of the invention. The concentrates generally contain less than about 50%, preferably less than about 25%, more preferably less than about 15%, and still more preferably less than about 6% hydrocarbon oil. The water-based functional fluids generally contain less than about 15%, preferably less than about 5%, and more preferably less than about 2% hydrocarbon oil.

These concentrates and water-based functional fluids can optionally include other conventional additives commonly employed in water-based functional fluids. These other additives include surfactants; thickeners; oil-soluble, water-insoluble functional additives such as antiwear agents, extreme pressure agents, dispersants, etc.; and supplemental additives such as corrosion-inhibitors, shear stabilizing agents, bactericides, dyes, water-softeners, odor masking agents, anti-foam agents and the like.

The concentrates are analogous to the water-based functional fluids except that they contain less water and proportionately more of the other ingredients. The concentrates can be converted to water-based functional fluids by dilution with water. This dilution is usually done by standard mixing techniques. This is often a convenient procedure since the concentrate can be shipped to the point of use before additional water is added. Thus, the cost of shipping a substantial amount of the water in the final water-based functional fluid is saved. Only the water necessary to formulate the concentrate (which is determined primarily be ease of handling and convenience factors), need be shipped.

Generally these water-based functional fluids are made by diluting the concentrates with water, wherein the ratio of water to concentrate is usually in the range of about 80:20 to about 99:1 by weight. As can be seen when dilution is carried out within these ranges, the final water-based functional fluid contains, at most, an insignificant amount of hydrocarbon oil.

In various preferred embodiments of the invention, the water-based functional fluids are in the form of solutions while in other embodiments they are in the form of micelle dispersions or microemulsions which appear to be true solutions. Whether a solution, micelle dispersion or microemulsion is formed is dependent, inter alia, on the particular components employed.

Also included within this invention are methods for preparing aqueous compositions, including both concentrates and water-based functional fluids, containing other conventional additives commonly employed in water-based functional fluids. These methods comprise the steps of:

(1) mixing at least one salt or complex additive of the invention with such other conventional additives either simultaneously or sequentially to form a dispersion or solution; optionally (2) combining said dispersion or solution with water to form said aqueous concentrate; and/or (3) diluting said dispersion or solution, or concentrate with water wherein the total amount of water used is in the amount required to provide the desired concentration of the components of the invention and other functional additives in said concentrates or said water-based functional fluids.

These mixing steps are preferably carried out using conventional equipment and generally at room or slightly elevated temperatures, usually below 100° C. and often below 50° C. As noted above, the concentrate can be formed and then shipped to the point of use where it is diluted with water to form the desired water-based functional fluid. In other instances, the finished water-based functional fluid can be formed directly in the same equipment used to form the concentrate or the dispersion or solution.

The surfactants that are useful in the aqueous compositions of the invention can be of the cationic, anionic, nonionic or amphoteric type. Many such surfactants of each type are know to the art. See, for example, McCutcheon's "Emulsifiers & Detergents", 1981, North American Edition, published by McCutcheon Division, MC Publishing Co., Glen Rock, N.J., U.S.A., which is hereby incorporated by reference for its disclosures in this regard.

Among the nonionic surfactant types are the alkylene oxide-treated products, such as ethylene oxide-treated phenols, alcohols, esters, amines and amides. Ethylene oxide/propylene oxide block copolymers are also useful nonionic surfactants. Glycerol esters and sugar esters are also known to be nonionic surfactants. A typical nonionic surfactant class useful with the present invention are the alkylene oxide-treated alkyl phenols such as the ethylene oxide alkyl phenol condensates sold by the Rohm & Haas Company. A specific example of these is Triton X-100 which contains an average of 9-10 ethylene oxide units per molecule, has an HLB value of about 13.5 and a molecular weight of about 628. Many other suitable nonionic surfactants are known; see, for example, the aforementioned McCutcheon's as well as the treatise "Non-Ionic Surfactants" edited by Martin J. Schick, M. Dekker Co., N.Y., 1967, which is herein incorporated by reference for its disclosures in this regard.

As noted above, cationic, anionic and amphoteric surfactants can also be used. Generally, these are all hydrophilic surfactants. Anionic surfactants contain negatively charged polar groups while cationic surfactants contain positively charged polar groups. Amphoteric dispersants contain both types of polar groups in the same molecule. A general survey of useful surfactants is found in Kirk-Othmer Encyclopedia of Chemical Technology, Second Edition, Volume 19, page 507 et seq. (1969, John Wiley and Son, New York) and the aforementioned compilation published under the name of McCutcheon's. These references are both hereby incorporated by reference for their disclosures relating to cationic, amphoteric and anionic surfactants.

Among the useful anionic surfactant types are the widely known carboxylate soaps, organo sulfates, sulfonates, sulfocarboxylic acids and their salts, and phosphates. Useful cationic surfactants include nitrogen compounds such as amine oxides and the well-known quaternary ammonium salts. Amphoteric surfactants include amino acid-type materials and similar types. Various cationic, anionic and amphoteric dispersants are available from the industry, particularly from such companies as Rohm & Haas and Union Carbide Corporation, both of America. Further information about anionic and cationic surfactants also can be found in the texts "Anionic Surfactants", Parts II and III, edited by W. M. Linfield, published by Marcel Dekker, Inc., New York, 1976, and "Cationic Surfactants", edited by E. Jungermann, Marcel Dekker, Inc., New York, 1976

Both of these references are incorporated by reference for their disclosures in this regard.

These surfactants, when used, are generally employed in effective amounts to aid in the dispersal of the various additives, particularly the functional additives discussed below, in the concentrates and water-based functional fluids of the invention. Preferably, the concentrates can contain up to about 75% by weight, more preferably from about 10% to about 75% by weight of one or more of these surfactants. The water-based functional fluids can contain up to about 15% by weight, more preferably from about 0.05% to about 15% by weight of one or more of these surfactants.

Often the aqueous compositions of this invention contain at least one thickener for thickening said compositions. Generally, these thickeners can be polysaccharides, synthetic thickening polymers, or mixtures of two or more of these. Among the poly-saccharides that are useful are natural gums such as those disclosed in "Industrial Gums" by Whistler and B. Miller, published by Academic Press, 1959. Disclosures in this book relating to water-soluble thickening natural gums in hereby incorporated by reference. Specific examples of such gums are gum agar, guar gum, gum arabic, algin, dextrans, xanthan gum and the like. Also among the polysaccharides that are useful as thickeners for the aqueous compositions of this invention are cellulose ethers and esters, including hydroxy hydrocarbyl cellulose and hydrocarbylhydroxy cellulose and its salts. Specific examples of such thickeners are hydroxyethyl cellulose and the sodium salt of carboxymethyl cellulose. Mixtures of two or more of any such thickeners are also useful.

It is a general requirement that the thickener used in the aqueous compositions of the present invention be soluble in both cold (10° C.) and hot (about 90° C.) water. This excludes such materials as methyl cellulose which is soluble in cold water but not in hot water. Such hot-water-insoluble materials, however, can be used to perform other functions such as providing lubricity to the aqueous compositions of this invention.

These thickeners can also be synthetic thickening polymers. Many such polymers are known to those of skill in the art. Representative of them are polyacrylates, polyacrylamides, hydrolyzed vinyl esters, water-soluble homo- and interpolymers of acrylamidoalkane sulfonates containing 50 mole percent at least of acryloamido alkane sulfonate and other comonomers such as acrylonitrile, styrene and the like. Poly-n-vinyl pyrrolidones, homo- and copolymers as well as water-soluble salts of styrene, maleic anhydride and isobutylene maleic anhydride copolymers can also be used as thickening agents.

Other useful thickeners are known to those of skill in the art and many can be found in the list in the aforementioned McCutcheon Publication: "Functional Materials", 1976, pp. 135–147, inclusive. The disclosures therein, relative to water-soluble polymeric thickening agents meeting the general requirements set forth above are hereby incorporated by reference.

Preferred thickeners, particularly when the compositions of the invention are required to be stable under high shear applications, are the water-dispersible reaction products formed by reacting at least one hydrocarbyl-substituted succinic acid and/or anhydride represented by the formula

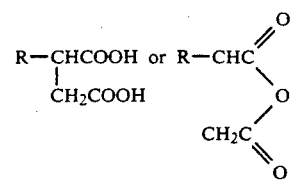

wherein R is a hydrocarbyl group of from about 8 to about 40 carbon atoms, with at least one water-dispersible amine terminated poly(oxyalkylene) or at least one water-dispersible hydroxy-terminated polyoxyalkylene. R preferably has from about 8 to about 30 carbon atoms, more preferably from about 12 to about 24 carbon atoms, still more preferably from about 16 to about 18 carbon atoms. In a preferred embodiment, R is represented by the formula

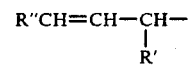

wherein R' and R" are independently hydrogen or straight chain or substantially straight chain hydrocarbyl groups, with the proviso that the total number of carbon atoms in R is within the above-indicated ranges. Preferably R' and R" are alkyl or alkenyl groups. In a particularly advantageous embodiment, R has from about 16 to about 18 carbon atoms, R' is hydrogen or an alkyl group of from 1 to about 7 carbon atoms or an alkenyl group of from 2 to about 7 carbon atoms, and R" is an alkyl or alkenyl group of from about 5 to about 15 carbon atoms.

The water-dispersible amine terminated poly(oxyalkylene)s are preferably alpha omega diamino poly(oxyethylene)s, alpha omega diamino poly(oxypropylene) poly(oxyethylene) poly(oxypropylene)s or alpha omega diamino propylene oxide capped poly(oxyethylene)s. The amine-terminated poly(oxyalkylene) can also be a urea condensate of such alpha omega diamino poly(oxytheylene)s, alpha omega diamino poly(oxypropylene) poly(oxyethylene) poly(oxypropylene)s or alpha omega diamino propylene oxide capped poly(oxyethylene)s. The amine-terminated poly(oxyalkylene) can also be a polyamine (e.g., triamino, tetramino, etc.) polyoxyalkylene provided it is amine-terminated and it is water-dispersible.

Examples of water-dispersible amine-terminated poly(oxyalkylene)s that are useful in accordance with the present invention are disclosed in U.S. Pat. Nos. 3,021,232; 3,108,011; 4,444,566; and RE 31,522. The disclosures of these patents are incorporated herein by reference. Water-dispersible amine terminated poly(oxyalkylene)s that are useful are commercially available from the Texaco Chemical Company under the trade name "Jeffamine".

The water-dispersible hydroxy-terminated polyoxyalkylenes are constituted of block polymers of propylene oxide and ethylene oxide, and a nucleus which is derived from organic compounds containing a plurality of reactive hydrogen atoms. The block polymers are attached to the nucleus at the sites of the reactive hydrogen atoms. Examples of these compounds include the hydroxy-terminated polyoxyalkylenes which are represented by the formula

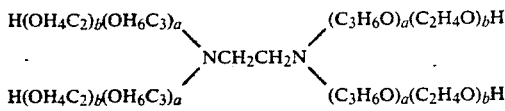

wherein a and b are integers such that the collective molecular weight of the oxypropylene chains range from about 900 to about 25,000, and the collective weight of the oxyethylene chains constitute from about 20% to about 90%, preferably from about 25% to about 55% by weight of the compound. These compounds are commercially available from BASF Wyandotte Corporation under the trade name "Tetronic". Additional examples include the hydroxy-terminated polyoxyalkylenes represented by the formula $$HO(C_2H_4O)_x(C_3H_6O)_y(C_2H_4O)_zH$$

wherein y is an integer such that the molecular weight of the oxypropylene chain is at least about 900, and x and z are integers such that the collective weight of the oxyethylene chains constitute from about 20% to about 90% by weight of the compound. These compounds preferably have a molecular weight in the range of about 1,100 to about 14,000. These compounds are commercially available from BASF Wyandotte Corporation under the trade name "Pluronic". Useful hydroxy-terminated polyoxyalkylenes are disclosed in U.S. Pat. Nos. 2,674,619 and 2,979,528, which are incorporated herein by reference.

The reaction between the carboxylic agent and the amine- or hydroxy-terminated polyoxyalkylene can be carried out at a temperature ranging from the highest of the melt temperatures of the reaction components up to the lowest of the decomposition temperatures of the reactioN components or products. Generally, the reaction is carried out at a temperature in the range of about 60° C. to about 160° C., preferably about 120° C. to about 160° C. The ratio of equivalents of carboxylic agent to polyoxyalkylene preferably ranges from about 0.1:1 to about 8:1, preferably about 1:1 to about 4:1, and advantageously about 2:1. The weight of an equivalent of the carboxylic agent can be determined by dividing its molecular weight by the number of carboxylic functions present. The weight of an equivalent of the amine-terminated polyoxyalkylene can be determined by dividing its molecular weight by the number of terminal amine groups present. The weight of an equivalent of the amine-terminated polyoxyalkylene can be determined by dividing its molecular weight by the number of terminal amine groups present. The number of terminal amine and hydroxyl groups can usually be determined from the structural formula of the polyoxyalkylene or empirically through well-known procedures. The amine/acids and ester/acids formed by the reaction of the carboxylic agent and amine-terminated or hydroxy-terminated polyoxyalkylene can be neutralized with, for example, one or more alkali metals, one or more amines, or a mixture thereof, and thus converted to amide/salts or ester/salts, respectively. Additionally, if these amide/acids or ester/acids are added to concentrates or functional fluids containing alkali metals or amines, amide/salts or ester/salts usually form, in situ.

South African Patent 85/0978 is incorporated herein by reference for its teachings with respect to the use of hydrocarbyl-substituted succinic acid or anhydride/hydroxy-terminated poly(oxyalkylene) reaction products as thickeners for aqueous compositions.

When the thickener is formed using an amine-terminated poly(oxyalkylene), the thickening characteristics of said thickener can be enhanced by combining it with at least one surfactant. Any of the surfactants identified above under the subtitle "Surfactants" can be used in this regard. When such surfactants are used, the weight ratio of thickener to surfactant is generally in the range of from about 1:5 to about 5:1, preferably from about 1:1 to about 3:1.

Typically, the thickener is present in a thickening amount in the aqueous compositions of this invention. When used, the thickener is preferably present at a level of up to about 70% by weight, preferably from about 20% to about 50% by weight of the concentrates of the invention. The thickener is preferably present at a level in the range of from about 1.5% to about 10% by weight, preferably from about 3% to about 6% by weight of the functional fluids of the invention.

The functional additives that can be used in the aqueous systems are typically oil-soluble, water-insoluble additives which function in conventional oil-based systems as extreme pressure agents, antiwear agents, load-carrying agents, dispersants, friction modifiers, lubricity agents, etc. They can also function as anti-slip agents, film formers and friction modifiers. As is well known, such additives can function in two or more of the abovementioned ways; for example, extreme pressure agents often function as load-carrying agents.

The term "oil-soluble, water-insoluble functional additive" refers to a functional additive which is not soluble in water above a level of about 1 gram per 100 milliliters of water at 25° C., but is soluble in mineral oil to the extent of at least 1 gram per liter at 25° C.

These functional additives can also include certain solid lubricants such as graphite, molybdenum disulfide and polytetrafluoroethylene and related solid polymers.

These functional additives can also include frictional polymer formers. Briefly, these are potential polymer forming materials which are dispersed in a liquid carrier at low concentration and which polymerize at rubbing or contacting surfaces to form protective polymeric films on the surfaces. The polymerizations are believed to result from the heat generated by the rubbing and, possibly, from catalytic and/or chemical action of the freshly exposed surface. A specific example of such materials is dilinoleic acid and ethylene glycol combinations which can form a polyester frictional polymer film. These materials are known to the art and descriptions of them are found, for example, in the journal "Wear", Volume 26, pages 369-392, and West German Published Patent Application 2,339,065. These disclosures are hereby incorporated by reference for their discussions of frictional polymer formers.

Typically these functional additives are known metal or amine salts of organo sulfur, phosphorus, boron or carboxylic acids which are the same as or of the same type as used in oil-based fluids. Typically such salts are of carboxylic acids of 1 to 22 carbon atoms including both aromatic and aliphatic acids; sulfur acids such as alkyl and aromatic sulfonic acids and the like; phosphorus acids such as phosphoric acid, phosphorus acid, phosphinic acid, acid phosphate esters and analogous sulfur homologs such as the thiophosphoric and dithiophosphoric acid and related acid esters; boron acids include boric acid, acid borates and the like. Useful functional additives also include metal dithiocarbamates such as molybdenum and antimony dithiocarbamates; as well as dibutyl tin sulfide, tributyl tin oxide, phosphates and phosphites; borate amine salts, chlorinated waxes; trialkyl tin oxide, molybdenum phosphates, and chlorinated waxes.

Many such functional additives are known to the art. For example, descriptions of additives useful in conventional oil-based systems and in the aqueous systems of this invention are found in "Advances in Petroleum Chemistry and Refining", Volume 8, edited by John J. McKetta, Interscience Publishers, N.Y., 1963, pages 31-38 inclusive; Kirk-Othmer "Encyclopedia of chemical Technology", Volume 12, Second Edition, Interscience Publishers, N.Y., 1967, page 575 et seq.; "Lubricant Additives" by M. W. Ranney, Noyes Data Corporation, Park Ridge, N.J., U.S.A., 1973; and "Lubricant Additives" by C. V. Smalheer and R. K. Smith, The Lezius-Hiles Co., Cleveland, Ohio, U.S.A. These references are hereby incorporated by reference for their disclosures of functional additives useful in the compositions of this invention.

In certain of the typical aqueous compositions of the invention, the functional additive is a sulfur or chlorosulfur extreme pressure agent, known to be useful in oil-base systems. Such materials include chlorinated aliphatic hydrocarbons, such as chlorinated wax; organic sulfides and polysulfides, such as benzyl-disulfide, bis-(chlorobenzyl)disulfide, dibutyl tetrasulfide, sulfurized sperm oil, sulfurized methyl ester of oleic acid, sulfurized alkylphenol, sulfurized dipentene, sulfurized terpene, and sulfurized Diels-Alder adducts; phosphosulfurized hydrocarbons, such as the reaction product of phosphorus sulfide with turpentine or methyl oleate; phosphorus esters such as the dihydrocarbon and trihydrocarbon phosphites, i.e., dibutyl phosphite, diheptyl phosphite, dicyclohexyl phosphite, pentylphenyl phosphite, dipentylphenyl phosphite, tridecyl phosphite, distearyl phosphite and polypropylene substituted phenol phosphite; metal thiocarbamates, such as zinc dioctyl-dithiocarbamate and barium heptylphenol dithiocarbamate; and Group II metal salts of a phosphorodithioic acid, such as zinc dicyclohexyl phosphorodithioate.

The functional additive can also be a film former such as a synthetic or natural latex or emulsion thereof in water. Such latexes include natural rubber latexes and polystyrene butadienes synthetic latex.

The functional additive can also be an anti-chatter or anti-squawk agent. Examples of the former are the amide metal dithiophosphate combinations such as disclosed in West German Patent 1,109,302; amine salt-azomethene combinations such as disclosed in British Patent Specification 893,977; or amine dithiophosphate such as disclosed in U.S. Pat. No. 3,002,014. Examples of anti-squawk agents are N-acyl-sarcosines and derivatives thereof such as disclosed in U.S. Pat. Nos. 3,156,652 and 3,156,653; sulfurized fatty acids and esters thereof such as disclosed in U.S. Pat. Nos. 2,913,415 and 2,982,734; and esters of dimerized fatty acids such as disclosed in U.S. Patent 3,039,967. The above-cited patents are incorporated herein by reference for their disclosure as pertinent to anti-chatter and anti-squawk agents useful as a functional additive in the aqueous systems of the present invention.

Specific examples of functional additives useful in the aqueous systems of this invention include the following commercially available products.

TABLE IV

| Functional Additive Trade Name | Chemical Description | Supplier |
|---|---|---|
| Anglamol 32 | Chlorosulfurized hydrocarbon | Lubrizol[1] |
| Anglamol 75 | Zinc dialkyl phosphate | Lubrizol[1] |
| Molyvan L | A thiaphosphomolybdate | Vanderbilt[2] |
| Lubrizol-5315 | Sulfurized cyclic carboxylate ester | Lubrizol |
| Emcol TS 230 | Acid phosphate ester | Witco[3] |

[1] The Lubrizol Corporation, Wickliffe, Ohio, U.S.A.
[2] R. T. Vanderbilt Company, Inc., New York, New York, U.S.A.
[3] Witco Chemical Corp., Organics Division, Houston, Texas, U.S.A.

Mixtures of two or more of any of the afore-described functional additives can also be used.

Typically, a functionally effective amount of the functional additive is present in the aqueous compositions of this invention.

The term "functionally effective amount" refers to a sufficient quantity of an additive to impart desired properties intended by the addition of said additive. For example, if an additive is a rust-inhibitor, a functionally effective amount of said rust-inhibitor would be an amount sufficient to increase the rust-inhibiting characteristics of the composition to which it is added. Similarly, if the additive is an antiwear agent, a functionally effective amount of said antiwear agent would be a sufficient quantity of the antiwear agent to improve the antiwear characteristics of the composition to which it is added.

The aqueous systems of this invention often contain at least one inhibitor for corrosion of metals. These inhibitors can prevent corrosion of either ferrous or non-ferrous metals (e.g., copper, bronze, brass, titanium, aluminum and the like) or both. The inhibitor can be organic or inorganic in nature. Usually it is sufficiently soluble in water to provide a satisfactory inhibiting action though it can function as a corrosion-inhibitor without dissolving in water, it need not be water-soluble. Many suitable inorganic inhibitors useful in the aqueous systems of the present invention are known to those skilled in the art. Included are those described in "Protective Coatings for Metals" by Burns and Bradley, Reinhold Publishing Corporation, Second Edition, Chapter 13, pages 596-605. This disclosure relative to inhibitors are hereby incorporated by reference. Specific examples of useful inorganic inhibitors include alkali metal nitrites, sodium di- and tripolyphosphate, potassium and dipotassium phosphate, alkali metal borate and mixtures of the same. Many suitable organic inhibitors are known to those of skill in the art. Specific examples include hydrocarbyl amine and hydroxy-substituted hydrocarbyl amine neutralized acid compound, such as neutralized phosphates and hydrocarbyl phosphate esters, neutralized fatty acids (e.g., those having about 8 to about 22 carbon atoms), neutralized aromatic carboxylic acids (e.g., 4-tertiarybutyl benzoic acid), neutralized naphthenic acids and neutralized hydrocarbyl sulfonates. Mixed salt esters of alkylated succinimides are also useful. Particularly useful amines include the alkanol amines such as ethanol amine, diethanolamine. Mixtures of two or more of any of the afore-described corrosion-inhibitors can also be used. The corrosion-inhibitor is usually present in concentrations in which they are effective in inhibiting corrosion of metals with which the aqueous composition comes in contact.

Certain of the aqueous systems of the present invention (particularly those that are used in cutting or shaping of metal) can also contain at least one polyol with inverse solubility in water. Such polyols are those that become less soluble as the temperature of the water increases. They thus can function as surface lubricity agents during cutting or working operations since, as the liquid is heated as a result of friction between a metal workpiece and work tool, the polyol of inverse solubility "plates out" on the surface of the workpiece, thus improving its lubricity characteristics.

The aqueous systems of the present invention can also include at least one bactericide. Such bactericides are well known to those of skill in the art and specific examples can be found in the afore-mentioned McCutcheon publication "Functional Materials" under the heading "Antimicrobials" on pages 9-20 thereof. This disclosure is hereby incorporated by reference as it relates to suitable bactericides for use in the aqueous compositions or systems of this invention. Generally, these bactericides are water-soluble, at least to the extent to allow them to function as bactericides.

The aqueous systems of the present invention can also include such other materials as dyes, e.g., an acid green dye; water softeners, e.g., ethylene diamine tetraacetate sodium salt or nitrilo triacetic acid; odor masking agents, e.g., citronella, oil of lemon, and the like; and anti-foamants, such as the well-known silicone anti-foamant agents.

The aqueous systems of this invention may also include an antifreeze additive where it is desired to use the composition at a low temperature. Materials such as ethylene glycol and analogous polyoxyalkylene polyols can be used as antifreeze agents. Clearly, the amount used will depend on the degree of antifreeze protection desired and will be known to those of ordinary skill in the art.

It should also be noted that many of the ingredients described above for use in making the aqueous systems of this invention are industrial products which exhibit or confer more than one property on such aqueous compositions. Thus, a single ingredient can provide several functions thereby eliminating or reducing the need for some other additional ingredient. Thus, for example, an extreme pressure agent such as tributyl tin oxide can also function as a bactericide.

While the invention has been described and illustrated with reference to certain preferred embodiments thereof, those skilled in the art will appreciate that various changes, modifications and substitutions can be made therein without departing from the spirit of the invention. For example, different concentration ranges other than the preferred ranges set forth hereinabove may be applicable as a consequence of variations in the oil base stock or the type of engine or the like. It is intended, therefore, that the invention be limited only by the scope of the claims which follow.

What is claimed is:

1. A method for preparing a basic metal dihydrocarbylphosphorodithioate wherein said method comprises reacting:
   (A) at least one dihydrocarbyl phopsphorodithioic acid or the normal or acid metal salt thereof; with
   (B) at least one metal oxide or hydroxide wherein the metal is zinc, copper, nickel, chromium, iron, cobalt, manganese, calcium, barium, antimony, lead, aluminum or tin; in the presence of
   (C) at least one catalyst, said catalyst being at least one alkali or alkaline-earth metal hydroxide, oxide, carbonate, halide or mixture thereof;
   wherein the metal of (C) is different from the metal of (A) or (B) and is not present in said basic metal dihydrocarbyl phosphorodithioate.

2. The method according to claim 1 wherein each of the hydrocarbyl groups of said dihydrocarbyl phosphorodithioic acid or salt thereof is, independently, a linear or branched alkyl group of 1 to about 200 carbon atoms, or a substituted or unsubstituted aryl group of about 6 to about 50 carbon atoms.

3. The method according to claim 1 wherein said metal of (A), (B) or both (A) and (B) is zinc, copper, calcium, cobalt or a mixture thereof.

4. The method according to claim 1 wherein the total number of carbon atoms in said dihydrocarbyl phosphorodithioic acid or salt is at least 8 carbon atoms.

5. The method according to claim 1 wherein each of the alkyl or aryl groups is, independently, selected from the group consisting of butyl, propyl, pentyl, hexyl, heptyl, octyl, oleyl, heptylphenyl, nonylphenyl, dodecylphenyl, cresyl and isomers thereof.

6. The method according to claim 1 wherein (C) is sodium hydroxide or potassium hydroxide.

7. The method according to claim 1 wherein (C) is sodium hydroxide.

8. A basic multiple metal complex of dihydrocarbyl phosphorodithioic acid represented by the formula

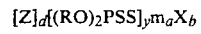

wherein M and X are different metal cations and each is selected from the group consisting of zinc, copper, nickel, chromium, iron, cobalt, manganese, calcium, barium, lead, tin, antimony and aluminum; Z is an anion selected from the group consisting of oxygen, hydroxide and carbonate; each R is hydrocarbyl; a and b are integers of at least 1; y is an integer which is dependent upon the oxidation states of M and X; and d is 1 or 2.

9. The complex according to claim 8 wherein the total number of carbon atoms in both R groups is at least 8 carbon atoms.

10. The complex according to claim 8 wherein each of said R groups is, independently, selected from the group consisting of propyl, butyl, pentyl, octyl, hexyl, heptyl, oleyl, heptylphenyl, nonylphenyl, dodecylphenyl, cresyl, isooctyl, isopropyl, 4-methyl-2-pentyl, and isomers thereof.

11. The complex according to claim 8 wherein M and X, independently, are selected from the group consisting of zinc, copper, calcium, cobalt and mixtures thereof.

12. The complex according to claim 8 wherein either M or X is zinc and the other is copper.

13. The complex according to claim 8 wherein each hydrocarbyl is, independently, a linear or branched alkyl group of 1 to about 200 carbon atoms or a substituted or unsubstituted aryl group of 6 to about 50 carbon atoms.

14. The complex according to claim 8 wherein M is zinc, X is copper, Z is oxygen, a is 3; b is 1; y is 6; and d is 1.

15. A lubricating composition comprising a major amount of an oil of lubricating viscosity and a minor antiwear or antioxidant amount of a complex of claim 8.

16. A grease composition comprising a major amount of an oil of lubrication viscosity, a minor thickening amount of a thickening agent and a minor antiwear or antioxidant amount of a complex of claim 8.

17. An aqueous functional fluid comprising a major amount of water and a minor antiwear or antioxidant amount of a complex of claim 8.

18. A concentrate for formulating lubricating compositions comprising a normally liquid, substantially inert organic solvent or diluent and from about 1% to about 99% by weight of a complex defined in claim 8.

19. A basic metal salt or a basic multiple metal complex of dihydrocarbylphosphorodithioic acid wherein said salt or complex is the reaction product of:
(A) at least one dihydrocarbyl phosphorodithioic acid or a normal or acid metal salt thereof; with
(B) at least one metal oxide or hydroxide wherein the metal is zinc, copper, nickel, chromium, iron, cobalt, manganese, calcium, barium, antimony, lead, aluminum or tin; in the presence of
(C) at least one catalyst, said catalyst being at least one alkali or alkaline-earth metal hydroxide, oxide, carbonate, halide or mixture thereof;
wherein the metal of (C) is different from the metal of (A) or (B) and is not present in said basic metal salt or basic multiple metal complex of dihydrocarbyl phosphorodithioic acid.

20. The salt or complex according to claim 19 wherein each hydrocarbyl group of said dihydrocarbylphosphorodithioic acid is independently selected from the group consisting of octyl, butyl, pentyl, propyl, hexyl, oleyl, heptyl, heptylphenyl, nonylphenyl, dodecylphenyl, cresyl, isooctyl, isopropyl, 4-methyl-2-pentyl, and the isomers thereof.

21. The salt or complex according to claim 19 wherein the metals of (A), (B) or both (A) and (B) are selected from the group consisting of zinc, copper, calcium and cobalt.

22. The salt or complex according to claim 19 wherein one of the metals of (A) and (B) is zinc and the other is copper.

23. The complex according to claim 14 wherein (C) is sodium hydroxide.

24. A lubricating composition comprising a major amount of an oil of lubricating viscosity and a minor antiwear or antioxidant amount of a salt or complex of claim 19.

25. A concentrate for formulating lubricating compositions comprising a normally liquid, substantially inert organic solvent or diluent and from about 1% to about 99% by weight of a salt or complex defined in claim 19.

26. A grease composition comprising a major amount of an oil of lubricating viscosity, a minor thickening amount of a thickening agent and a minor antiwear or antioxidant amount of a salt or complex of claim 19.

27. An aqueous functional fluid comprising a major amount of water and a minor antiwear or antioxidant amount of a salt or complex of claim 19.

28. A method for preparing a basic metal dihydrocarbylphosphordithioate comprising reacting:
(A) at least one normal or acid metal dihydrocarbylphosphorodithioate, the total number of carbon atoms in said dihydrocarbylphosphorodithioate being at least 8; with
(B) at least one metal oxide;
in the absence of a catalyst; wherein said metals of (A) and (B) are the same or different and are selected from the group consisting of zinc, copper, nickel, chromium, iron, cobalt, manganese, calcium, barium, lead, antimony, tin and aluminum.

29. The method according to claim 28 wherein the metals of (A), (B) or both (A) and (B) are selected from the group consisting of zinc, copper, calcium and cobalt.

30. The method according to claim 28 wherein each hydrocarbyl group of said dihydrocarbyl phosphorodithioate is, independently, a linear or branched alkyl group of 1 to about 200 carbon atoms, or a substituted or unsubstituted aryl group of about 6 to about 50 carbon atoms.

31. The method according to claim 30 wherein each hydrocarbyl group is a substituted or unsubstituted aryl of 6 to about 50 carbon atoms or alkyl of greater than 24 carbon atoms.

32. The method according to claim 30 wherein the metals of (A) and (B) are different and selected from zinc and copper.

33. The method according to claim 28 wherein the metals of (A), (B) or both (A) and (B) are selected from the group consisting of zinc, copper, calcium and cobalt.

34. A method for preparing a basic metal dihydrocarbylphosphorodithioate wherein said method comprises reacting:
(A) at least one dihydrocarbyl phosphorodiothioic acid or the normal or acid metal salt thereof, the total number of carbon atoms in said dihydrocarbyl phosphorodithioic acid or salt being at least 8; with
(B) at least one metal oxide or hydroxide wherein the metal is selected from the group consisting of zinc, copper, nickel, chromium, iron, cobalt, manganese, calcium, barium, antimony, lead, aluminum, and tin; in the presence of
(C) at least one catalyst, said catalyst being at least one alkali or alkaline-earth metal hydroxide, oxide, carbonate, halide or mixture thereof;
wherein the metal of (C) is different from the metal of (A) or (B) and is not present in said basic metal dihydrocarbyl phosphorodiothioate.

35. The method according to claim 34 wherein each alkyl or aryl group is, independently, selected from the group consisting of butyl, propyl, pentyl, hexyl, heptyl, octyl, oleyl, heptylphenyl, nonylphenyl, dodecylphenyl, cresyl and isomers thereof.

36. A basic multiple metal complex of dihydrocarbyl phosphorodithioic acid represented by the formula

wherein M and X are different metal cations and each is selected from the group consisting of zinc, copper, nickel, chromium, iron, cobalt, manganese, calcium, barium, lead, tin, antimony and aluminum; Z is an anion selected from the group consisting of oxygen, hydroxide and carbonate; each R is hydrocarbyl, the total number of carbon atoms in both R groups being at least 8 carbon atoms; a and b are integers of at least 1; y is an integer which is dependent upon the oxidation states of M and X; and d is 1 or 2.

37. A basic metal salt or a basic multiple metal complex of dihydrocarbylphosphorodithioic acid wherein said salt or complex is the reaction product of:

(A) dihydrocarbyl phosphorodithioic acid or a normal or acid metal salt thereof, the total number of carbon atoms in said dihydrocarbyl phosphorodithioic acid or salt being at least 8 carbon atoms; with (B) at least one metal oxide or hydroxide wherein the metal is selected from the group consisting of zinc, copper, nickel, chromium, iron, cobalt, manganese, calcium, barium, antimony, lead, aluminum and tin; in the presence of (C) at least one catalyst, said catalyst being at least one alkali or alkaline-earth metal hydroxide, oxide, carbonate, halide or mixture thereof;

(D) wherein the metal of (C) is different from the metal of (A) or (B) and is not present in said basic metal salt or basic multiple metal complex of dihydrocarbyl phosphorodiothioc acid.

38. A method for preparing a basic metal dihydrocarbylphosphorodithioate wherein the metal is zinc, copper or a mixture thereof, said method comprising reacting:

(A) at least one dihydrocarbyl phosphorodithioic acid or the normal or acid metal salt thereof, said metal being zinc, copper or a mixture thereof; with (B) at least one metal oxide or hydroxide wherein the metal is zinc, copper or a mixture thereof; in the presence of (C) at least one catalyst, said catalyst being at least one alkali or alkaline-earth metal hydroxide, oxide, carbonate, halide or mixture thereof.

39. A basic multiple metal complex of dihydrocarbyl phosphorodithioic acid represented by the formula $$[Z]_d[(RO)_2PSS]_y M_a X_b$$

wherein M or X is zinc and the other is copper; Z is an anion selected from the group consisting of oxygen, hydroxide and carbonate; each R is hydrocarbyl; a and b are integers of at least 1; y is an integer which is dependent upon the oxidation states of M and X; and d is 1 or 2.

40. A basic zinc or copper salt, or a basic multiple metal complex of dihydrocarbylphosphorodithioic acid wherein the metals are zinc and copper, said salt or complex being the reaction product of:

(A) at least one dihydrocarbyl phosphorodiothioic acid, or a normal or acid metal salt thereof, said metal being zinc, copper or a mixture thereof; with (B) at least one metal oxide or hydroxide, said metal being zinc, copper or a mixture thereof; in the presence of (C) at least one catalyst, said catalyst being at least one alkali or alkaline-earth metal hydroxide, oxide, carbonate, halide or mixture thereof.

41. A method for preparing a basic metal dihydrocarbylphosphorodithioate comprising reacting:

(A) at least one normal or acid metal dihydrocarbylphosphorodithioate, the total number of carbon atoms in said dihydrocarbylphosphorodithioate being at least 8 carbon atoms; with (B) at least one metal oxide;

in the absence of a catalyst; wherein said metals of (A) and (B) are the same or different and are selected from the group consisting of zinc and copper.

* * * * *